US009788761B2

United States Patent
Lu et al.

(10) Patent No.: US 9,788,761 B2
(45) Date of Patent: Oct. 17, 2017

(54) MOTION CORRECTION FOR MAGNETIC RESONANCE ANGIOGRAPHY (MRA) WITH 3D RADIAL ACQUISITIONS

(71) Applicant: TOSHIBA MEDICAL SYSTEMS CORPORATION, Tokyo (JP)

(72) Inventors: Aiming Lu, Chicago, IL (US); Cheng Ouyang, Buffalo Grove, IL (US)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 734 days.

(21) Appl. No.: 14/191,762

(22) Filed: Feb. 27, 2014

(65) Prior Publication Data

US 2015/0241538 A1    Aug. 27, 2015

(51) Int. Cl.
*G01R 33/48* (2006.01)
*A61B 5/11* (2006.01)
*G01R 33/565* (2006.01)
*A61B 5/026* (2006.01)
(Continued)

(52) U.S. Cl.
CPC .......... *A61B 5/1128* (2013.01); *A61B 5/0042* (2013.01); *A61B 5/0263* (2013.01); *A61B 5/7214* (2013.01); *G01R 33/4826* (2013.01); *G01R 33/56509* (2013.01); *G01R 33/56366* (2013.01)

(58) Field of Classification Search
CPC ... A61B 5/1128; A61B 5/0042; A61B 5/0263; A61B 5/7214; G01R 33/4826; G01R 33/56509; G01R 33/56366
See application file for complete search history.

(56) References Cited

U.S. PATENT DOCUMENTS

2009/0143666 A1*  6/2009  Edelman ............... A61B 5/055
                                                                     600/410
2009/0275822 A1* 11/2009  Detsky .................. A61B 5/055
                                                                     600/413
(Continued)

OTHER PUBLICATIONS

Barger et al., "Time-Resolved Contrast-Enhanced Imaging With Isotropic Resolution and Broad Coverage Using An Undersampled 3D Projection Trajectory", Magnetic Resonance in Medicine 48:297-305 (2002).
(Continued)

*Primary Examiner* — Clayton E Laballe
*Assistant Examiner* — Ruifeng Pu
(74) *Attorney, Agent, or Firm* — Nixon & Vanderhye P.C.

(57) ABSTRACT

A magnetic resonance imaging (MRI) system, method and/or computer readable medium is configured to effect magnetic resonance angiography (MRA) images with reduced motion artifacts includes acquiring a plurality of k-space data sets by traversing a plurality of radial trajectories in three-dimensional (3D) k-space, generating a plurality of 3D MR images derived from k-space populated by the k-space data sets, aligning the 3D MR images with respect to each other, determining one or more motion parameters for the object based upon the aligning, modifying values of k-space data sets using the determined one or more motion parameters, generating a motion-corrected 3D MR image from a combination of acquired k-space data sets including the modified values.

13 Claims, 5 Drawing Sheets

(51) Int. Cl.
*A61B 5/00* (2006.01)
*G01R 33/563* (2006.01)

(56) References Cited

U.S. PATENT DOCUMENTS

| | | | | |
|---|---|---|---|---|
| 2011/0260725 | A1* | 10/2011 | Mordini | G01R 33/56325 324/309 |
| 2012/0082355 | A1* | 4/2012 | Mendes | G01R 33/56509 382/131 |
| 2012/0243756 | A1* | 9/2012 | Samsonov | G01R 33/56509 382/131 |
| 2013/0119985 | A1* | 5/2013 | Lin | G01R 33/4818 324/309 |
| 2013/0257429 | A1* | 10/2013 | Edelman | G01R 33/5635 324/309 |
| 2013/0272591 | A1* | 10/2013 | Xue | G06T 11/003 382/131 |
| 2014/0009156 | A1* | 1/2014 | Doneva | G01R 33/5611 324/309 |
| 2014/0126796 | A1* | 5/2014 | Chesneau | G01R 33/4824 382/131 |
| 2016/0170001 | A1* | 6/2016 | Hanada | G01R 33/4824 324/322 |

OTHER PUBLICATIONS

Dai et al., "Continuous Flow-Driven Inversion for Arterial Spin Labeling Using Pulsed Radio Frequency and Gradient Fields", Magnetic Resonance in Medicine 60:1488-1497 (2008).

Wu et al., "Noncontrast-Enhanced Three-Dimensional (3D) Intracranial MR Angiography Using Pseudocontinuous Arterial Spin Labeling and Accelerated 3D Radial Acquisition", Magnetic Resonance in Medicine 69:708-715 (2013).

Woods et al., "Automated Image Registration: I. General Methods and Intrasubject, Intramodality Validation", J Comput Assist Tomogr. vol. 00 No. 0, 1998, pp. 1-14.

Woods et al., "Automated Image Registration: II. Intersubject Validation of Linear and Nonlinear Models", J Comput Assist Tomogr., vol. 22(1).Jan./Feb. 1998.153-165.

\* cited by examiner

MOTION CORRECTION FOR MAGNETIC RESONANCE ANGIOGRAPHY (MRA) WITH 3D RADIAL ACQUISITIONS

FIELD

The subject matter below relates generally to reducing motion artifacts in magnetic resonance imaging (MRI). In particular, the subject matter relates to reducing motion artifacts using three-dimensional (3D) radial acquisitions. In one example, the subject matter relates to reducing motion artifacts in MR images acquired by pseudo continuous arterial spin labeling (pCASL) magnetic resonance angiography (MRA).

DETAILED DESCRIPTION

Figure 1:
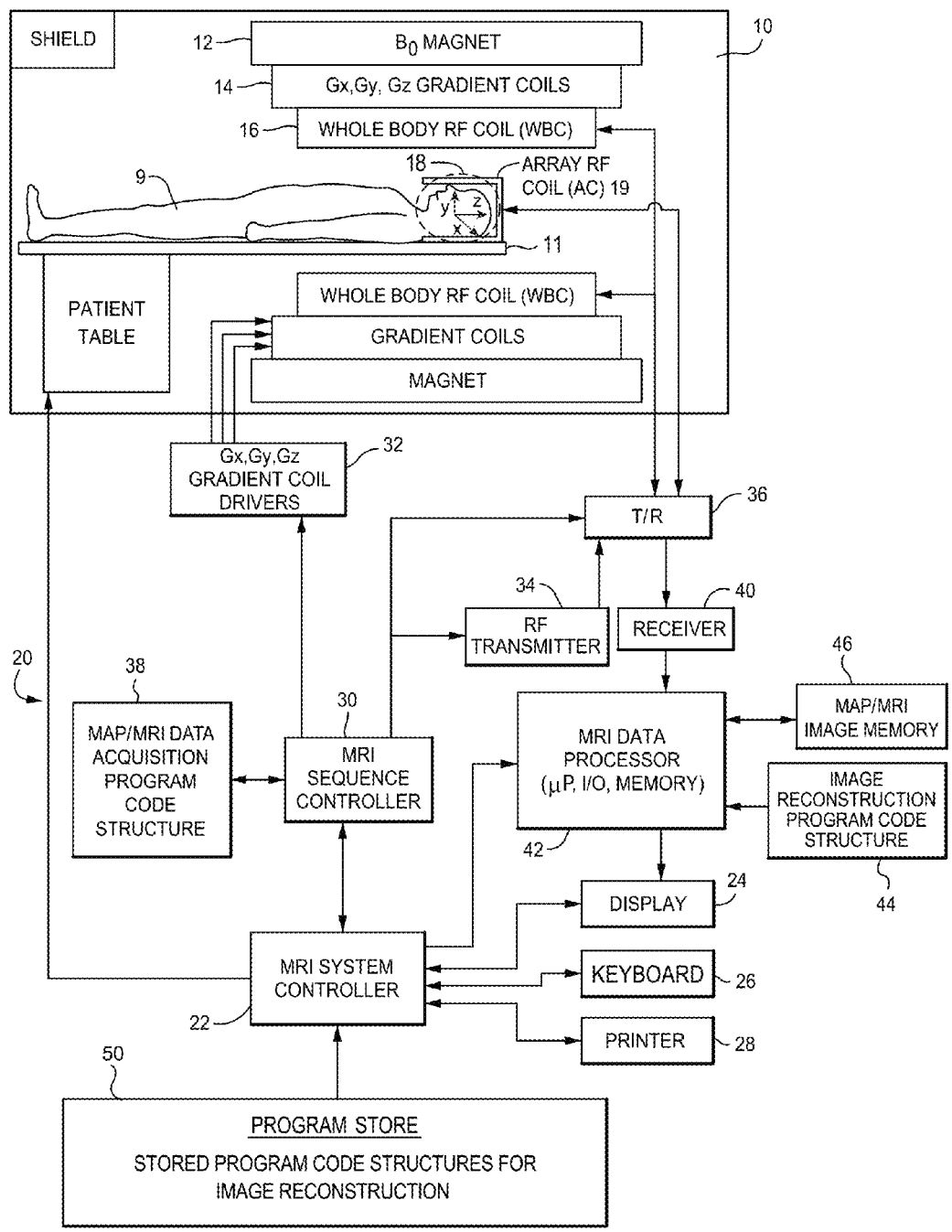
FIG. 1 is a high-level schematic block diagram of an MRI system adapted to reduce motion artifacts in MR images, in accordance with one or more embodiments.

The MRI system shown in FIG. 1 includes a gantry 10 (shown in schematic cross-section) and various related system components 20 interfaced therewith. At least the gantry 10 is typically located in a shielded room. The MRI system geometry depicted in FIG. 1 includes a substantially coaxial cylindrical arrangement of the static field $B_0$ magnet 12, a $G_x$, $G_y$, and $G_z$ gradient coil set 14 and a large whole body RF coil (WBC) assembly 16. Along the horizontal axis of this cylindrical array of elements is an imaging volume 18 shown as substantially encompassing the head of a patient 9 supported by a patient table 11. One or more smaller array RF coils 19 might be more closely coupled to the patient head (referred to herein, for example, as "scanned object" or "object") in imaging volume 18. As those in the art will appreciate, compared to the WBC (whole body coil), relatively small coils and/or arrays such as surface coils or the like are often customized for particular body parts (e.g., arms, shoulders, elbows, wrists, knees, legs, chest, spine, etc.). Such smaller RF coils are herein referred to as array coils (AC) or phased array coils (PAC). These may include at least one coil configured to transmit RF signals into the imaging volume and one or more receiver coils configured to receive RF signals from an object, such as the patient head in the example above, in the imaging volume.

An MRI system controller 22 has input/output ports connected to a display 24, keyboard 26 and printer 28. As will be appreciated, the display 24 may be of the touch-screen variety so that it provides control inputs as well. The display 24 may provide a user interface, such as a graphical user interface (GUI), for displaying output of the MRI system and/or for providing an interface for configuring various parameters for the operation of the MR imaging and image reconstruction.

The MRI system controller 22 interfaces with MRI sequence controller 30 which, in turn, controls the $G_x$, $G_y$, and $G_z$ gradient coil drivers 32, as well as the RF transmitter 34 and the transmit/receive switch 36 (if the same RF coil is used for both transmission and reception). The MRI sequence controller 30 includes suitable program code structure 38 for implementing MRI imaging (also known as nuclear magnetic resonance, or NMR, imaging) techniques such as, for example, and without limitation, parallel imaging and/or EPI imaging. Moreover, MRI sequence controller 30 may facilitate one or more preparation scan (prescan) sequences, and a scan sequence to obtain a main scan MR image (sometimes referred to as a diagnostic image). MR data from prescans may be used, for example, to determine sensitivity maps for RF coils 16 and/or 19 (sometimes referred to as coil sensitivity maps or spatial sensitivity maps), and to determine unfolding maps from parallel imaging.

The MRI system 20 includes an RF receiver 40 providing input to data processor 42 so as to create processed image data, which is sent to display 24. The MRI data processor 42 is also configured for access to previously generated MR data, images, and/or system configuration parameters 46 and MRI image reconstruction program code structures 44 and 50.

Also illustrated in FIG. 1 is a generalized depiction of an MRI system program store 50 where stored program code structures (e.g., for image reconstruction with reduced motion artifacts, for defining graphical user interfaces and accepting operator inputs to same, etc.) are stored in non-transitory computer-readable storage media accessible to the various data processing components of the MRI system. As those in the art will appreciate, the program store 50 may be segmented and directly connected, at least in part, to different ones of the system 20 processing computers having most immediate need for such stored program code structures in their normal operation (i.e., rather than being commonly stored and connected directly to the MRI system controller 22).

Indeed, as those in the art will appreciate, the FIG. 1 depiction is a very high-level simplified diagram of a typical MRI system with some modifications so as to practice exemplary embodiments described hereinbelow. The system components can be divided into different logical collections of "boxes" and typically comprise numerous digital signal processors (DSP), microprocessors and special purpose processing circuits (e.g., for fast A/D conversions, fast Fourier transforming, array processing, etc.). Each of those processors is typically a clocked "state machine" wherein the physical data processing circuits progress from one physical state to another upon the occurrence of each clock cycle (or predetermined number of clock cycles).

Not only does the physical state of processing circuits (e.g., CPUs, registers, buffers, arithmetic units, etc.) progressively change from one clock cycle to another during the course of operation, the physical state of associated data storage media (e.g., bit storage sites in magnetic storage media) is transformed from one state to another during operation of such a system. For example, at the conclusion of an image reconstruction process and/or sometimes a image reconstruction map (e.g., coil sensitivity map, unfolding map, ghosting map, a distortion map etc) generation process, an array of computer-readable accessible data value storage sites in physical storage media will be transformed from some prior state (e.g., all uniform "zero" values or all "one" values) to a new state wherein the physical states at the physical sites of such an array vary between minimum and maximum values to represent real world physical events and conditions (e.g., the internal physical structures of a patient over an imaging volume space). As those in the art will appreciate, such arrays of stored data values represent and also constitute a physical structure—as does a particular structure of computer control program codes that, when sequentially loaded into instruction registers and executed by one or more CPUs of the MRI system 20, causes a particular sequence of operational states to occur and be transitioned through within the MRI system.

The exemplary embodiments described herein provide for reducing motion artifacts in MRA images acquired by MR RF pulse sequences such as, for example, pCASL as described below. Although many of the embodiments described herein are directed to pCASL, the techniques described herein for reducing motion artifacts may also be applied to MRA images other than those acquired through pCASL. One or more embodiments include a novel technique for using motion artifacts determined based upon low resolution 3D images derived from 3D radial acquisitions, to correct k-space data in order to generate motion-corrected volume images.

MRI images are formed by acquiring RF response values (e.g. echo data) for points in k-space. For three dimensional (3D) MR images, the RF response values are generated by traversing k-space in three dimensions (e.g., along x, y and z axes) according to a configured MR RF pulse sequence.

Arterial spin labeling (ASL) is of particular interest for many MRA applications, including, for example, intracranial applications. ASL relies on the inflow of blood into the imaging volume; however, ASL uses separate sequences to label and image inflowing spins. By subtracting the images with different labeling sequences, angiographic images can be obtained with near zero background, vessel selectivity, and inflow dynamics. However, due to relatively low signal-to-noise ratio (SNR) and long scan times, the use of ASL for angiography in clinical environments has been limited.

ASL in MRI applications is typically considered in two variants: pulsed ASL (PASL) and continuous ASL (CASL). PASL uses a single inversion pulse and is highly sensitive to the selection of inversion time. CASL requires specialized hardware, for example, for continuous tagging.

pCASL (or, as noted above, pseudo continuous ASL) is a relatively recent variant of ASL, directed to overcome some of the deficiencies of PASL and CASL. pCASL utilizes flow-driven adiabatic inversion by discrete RF pulses to achieve high tagging efficiency of flowing spins and thus high SNR perfusion images compared to pulsed ASL (Dai et al., "Continuous Flow-Driven Inversion for Arterial Spin Labeling Using Pulsed Radio Frequency and Gradient Fields," Magnetic Resonance in Medicine, 60:1488-1497, 2008). Unlike CASL, pCASL does not require a continuous transmitter for contiguous tagging pulses. pCASL is of particular interests for MRA applications due to the near zero background obtained after subtracting the tagging image from the control image.

Radial acquisitions can be used in pCASL-based MRA applications, in order to obtain whole field-of-view (FOV) coverage within clinically acceptable scan time and submillimeter resolution. Wu et al., "Noncontrast-Enhanced Three-Dimensional (3D) Intracranial MR Angiography Using Pseudo continuous Arterial Spin Labeling and Accelerated 3D Radial Acquisition," Magnetic Resonance in Medicine, 69:708-715, 2013, which is hereby incorporated in its entirety by reference, describes an example radial acquisition technique for acquiring MR RF echo data for populating k-space. pCASL with 3D radial acquisition is substantially insensitive to $B_0$ inhomogeneity, and under sampling of k-space introduces diffuse and/or random low-level background noise rather than relatively more significant ghosting and/or aliasing artifacts caused by Cartesian acquisitions.

pCASL with 3D radial acquisition produces high quality non-contrast enhanced MRA images compared to other CASL techniques. To achieve the desired level of high resolution image with high SNR, the typical data acquisition time of pCASL with 3D radial acquisition with whole brain coverage is substantial improved over other 3D CASL acquisitions. This substantial reduction in acquisition time is due, at least in part, to the sparse image volume created by pCASL, and noise-like artifacts specific to 3D radial acquisition.

Although radial acquisition is relatively insensitive to object (e.g. patient) motion due to the oversampling of k-space center data, motion can still degrade image quality and can cause image blurring or distortion. Consequently, this compromises the application of pCASL with 3D radial acquisition in clinical settings.

Despite the use of various restraining systems, motion of the parts of the body being imaged, for example, the patient's head, is hard to prevent during long data acquisitions. Prevention of such motion may especially be difficult when considering the health conditions of the patients and the restrictive environment inside the scanner that may cause the patients to adjust their head positions etc. to relieve awkward pressure points.

In embodiments, a novel technique for pCASL with 3D radial acquisition that outputs motion-corrected images, and which also improves patient comfort, is provided.

In embodiments, the radial lines (e.g., radial trajectories of points in 3D k-space) that may be necessary to achieve the desired k-space coverage are divided into one or more subsets. The subsets may be separated by the pCASL labeling pulse (e.g. train of individual pulses) having a duration of several seconds (e.g., 3 s). Following the labeling, a data acquisition window of approximately is (of course, in embodiments, the actual duration may vary) allows for a subset of radial lines to be collected.

In some embodiments, the radial lines may be acquired in such a manner that following the pCASL labeling, each subset of radial lines are distributed evenly in the entire k-space, and/or any number of subsets of radial lines can be combined to cover the entire k-space approximately evenly and more densely. Algorithms such as, but not limited to, bit-reversal can be used in selecting radial lines for each subset.

A low resolution volume image may be generated from a subset of radial lines. In some embodiments, several consecutive subsets of radial lines are combined to generate a low resolution volume image. This process of low resolution image creation may be carried out for all subsets. The temporal resolution of the low resolution image volumes may be configurable, and may be as low as several seconds. The low resolution image volumes are then aligned in order to derive motion parameters (e.g., rotation, translation). The derived parameters are then used to modify k-space data, such that, the modified k-space data can be used to reconstruct a final motion-corrected image. The alignment can be performed on a per radial line basis.

Embodiments described herein may have several advantages over conventional pCASL techniques. For example, embodiments may provide improved robustness to motion during relatively long scan with motion correction without any time penalty, and may provide for improved subject comfort. The segmented acquisition scheme makes it possible for the subject to adjust his/her position if necessary with little or no impact on the quality of the final image. In some embodiments, dummy scan and/or time interval can be inserted between the acquisitions of two subsets of radial lines.

Figure 2:
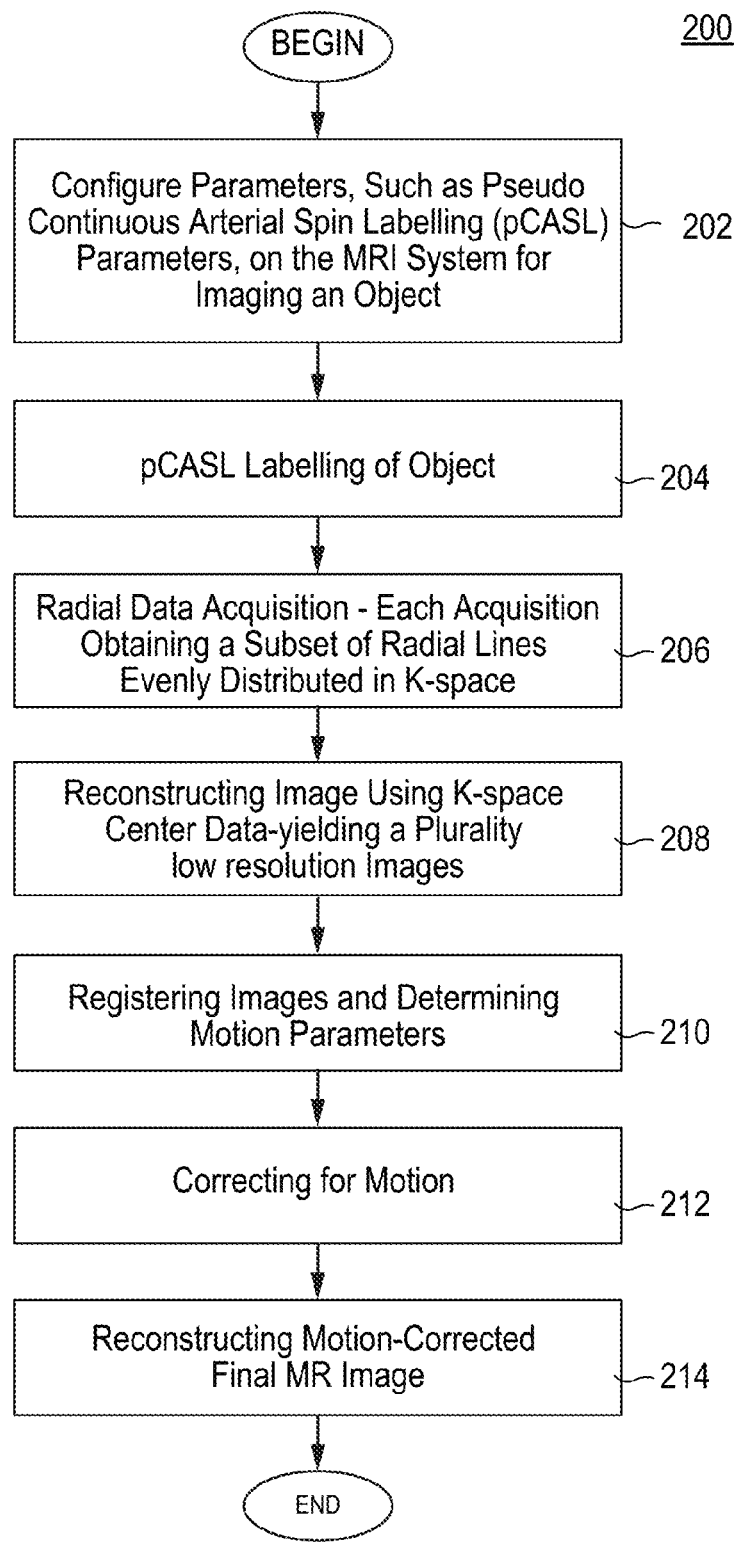
FIG. 2 illustrates a flowchart of a technique for reducing motion artifacts in MRA images acquired by pCASL, in accordance with one or more embodiments.

FIG. 2 illustrates a flowchart of a method 200 for reducing motion artifacts in MRA images acquired by pCASL, in accordance with one or more embodiments.

At operation 202, the MRI system is configured to acquire motion-corrected MRA images of an object. Operation 202 may include, for example, configuration of pCASL parameters and/or radial sampling parameters. pCASL parameters may include, for example, selection of pCASL control/label RF pulse sequence, duration of control/label pulse sequence, control/label pulse configuration (e.g. pulse width, pulse amplitude, pulse shape, inter-pulse gap, etc.). Radial sampling parameters may include, for example, the interleaving between radial lines, algorithm for selecting radial lines, etc. A configuration interface may also provide for configuring the motion parameters to be determined, volume image registration parameters, and the like.

At operation 204, a labeling radio frequency pulse sequence is performed. A labeling/control sequence such as that shown in FIG. 4, for example, sequence 404, may be applied to the imaged object at an appropriate labeling location, such as, for example, labeling plane 304 shown in FIG. 3.

At operation 206, 3D radial acquisition of k-space data is performed. After the labeling, and in some embodiments a time interval after the labeling, the acquisition of points in 3D k-space along radial trajectories is performed. An acquisition sequence such as sequence 402 shown in FIG. 4 may be used in the acquisition.

Each iteration of operations 204 and 206 acquires a subset of radial lines in the 3D k-space. Specifically, following a first invocation of operation 204 which labels blood that would flow in to the imaging region, a first invocation of operation 206 acquires an entire subset of radial lines of k-space data in 3D. Operations 204 and 206 are repeated for as many subsets of radial lines of k-space data as configured or previously set in the MRI system.

At operation 208, low resolution 3D MR images are reconstructed using the acquired subsets of radial lines. Specifically, the low resolution images are formed using the k-space center information. Conventional techniques may be used to reconstruct a low resolution image from center k-space information from each acquired subset of radial lines. In some embodiments, two or more of the acquired subsets may be combined to generate each low resolution image.

At operation 210, the plurality of 3D MR images are aligned (also referred to as "registered") with each other, and motion parameters are determined. Conventional techniques, such as, for example, the techniques described in Woods et al., "Automated Image Registration: I. General Methods and Intrasubject, Intramodality Validation," Journal of Computer Assisted Tomography, vol. 00, no. 0, pp. 1-14, 1998, and Woods et al., "Automated Image Registration: II. Intersubject Validation of Linear and Nonlinear Models," Journal of Computer Assisted Tomography, vol. 22 no. 1, pp. 153-155, 1998, both of which are hereby incorporated by reference in their entireties, can be used in aligning the 3D images. The alignment can be performed on a per radial line basis.

By aligning the 3D images, motion artifacts of the object with respect to each image can be identified. Specifically, for rigid motion, such as that may occur with head movements when the head is restrained in the MRI system, motion parameters such as rotation and translation can be determined with respect to the object, or points in the object.

At operation 212, motion parameters are determined from the low resolution source (before subtraction) label/control images with respect to a reference base image. For example, a temporally earlier occurring image is selected as the base image, and the motion parameters representing object motion artifacts in a later occurring (e.g., temporally next image) is used to correct k-space data corresponding to the base image. For example, rotation and/or translation of one or more pixels may be corrected in accordance with the determined motion parameters. It will be noted that, on a pixel-by-pixel basis, modifications based upon these parameters can be applied directly to corresponding k-space data.

At operation 214, a motion-corrected MR image is reconstructed using the motion-corrected k-space information. The motion-corrected image is of higher resolution than the low resolution images generated from center k-space information. The motion-corrected MR image may then be used for display to the user, may be stored in a data storage, may be transmitted to another location or device, and/or may be used in further processing.

Figure 3:
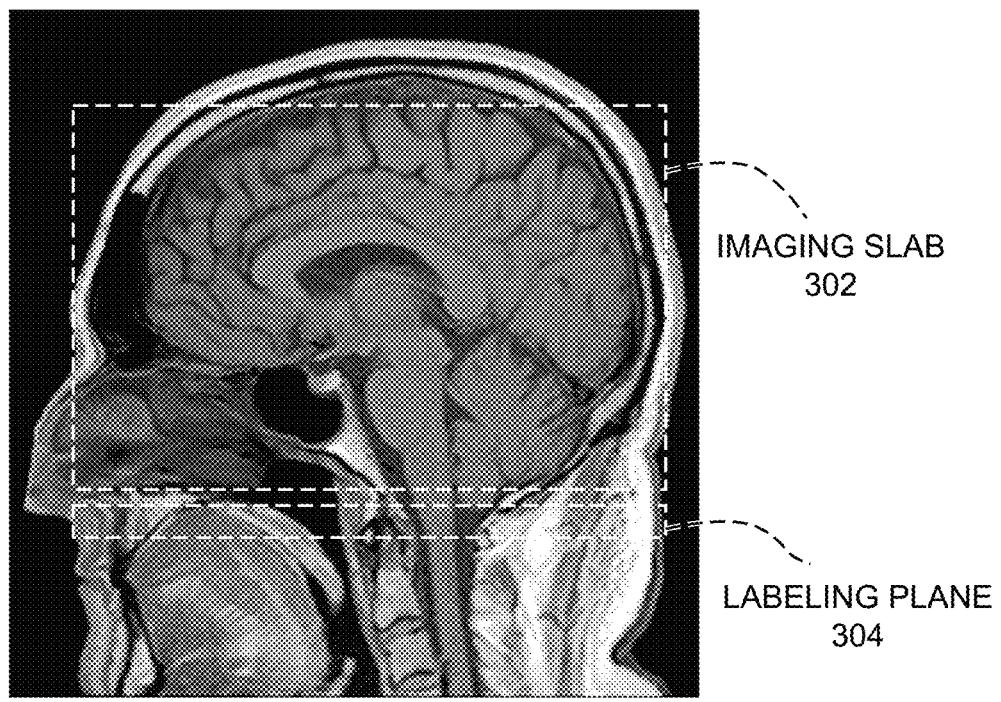
FIG. 3 illustrates an exemplary labeling plane and an imaging slab, in accordance with one or more embodiments.

FIG. 3 illustrates an exemplary labeling plane and an imaging slab, in accordance with one or more embodiments. An RF pulse sequence is used to label (i.e., tag) blood flowing through labeling plane 304. Data acquisition of the labeled (i.e., tagged) blood then takes place within the imaging slab 302. The size of labeling plane 304 and the size of the imaging slab 302 may be configurable. For example, in the example shown, the height of labeling plane 304 may be configured to cover a longer or shorter distance of arterial blood flow. Moreover, the spacing between labeling plane 304 and imaging slab 302 may also be configurable.

It will be understood that, in addition to the intracranial MRA application shown in FIG. 3, embodiments described herein are also applicable to other areas of the anatomy.

Figure 4:
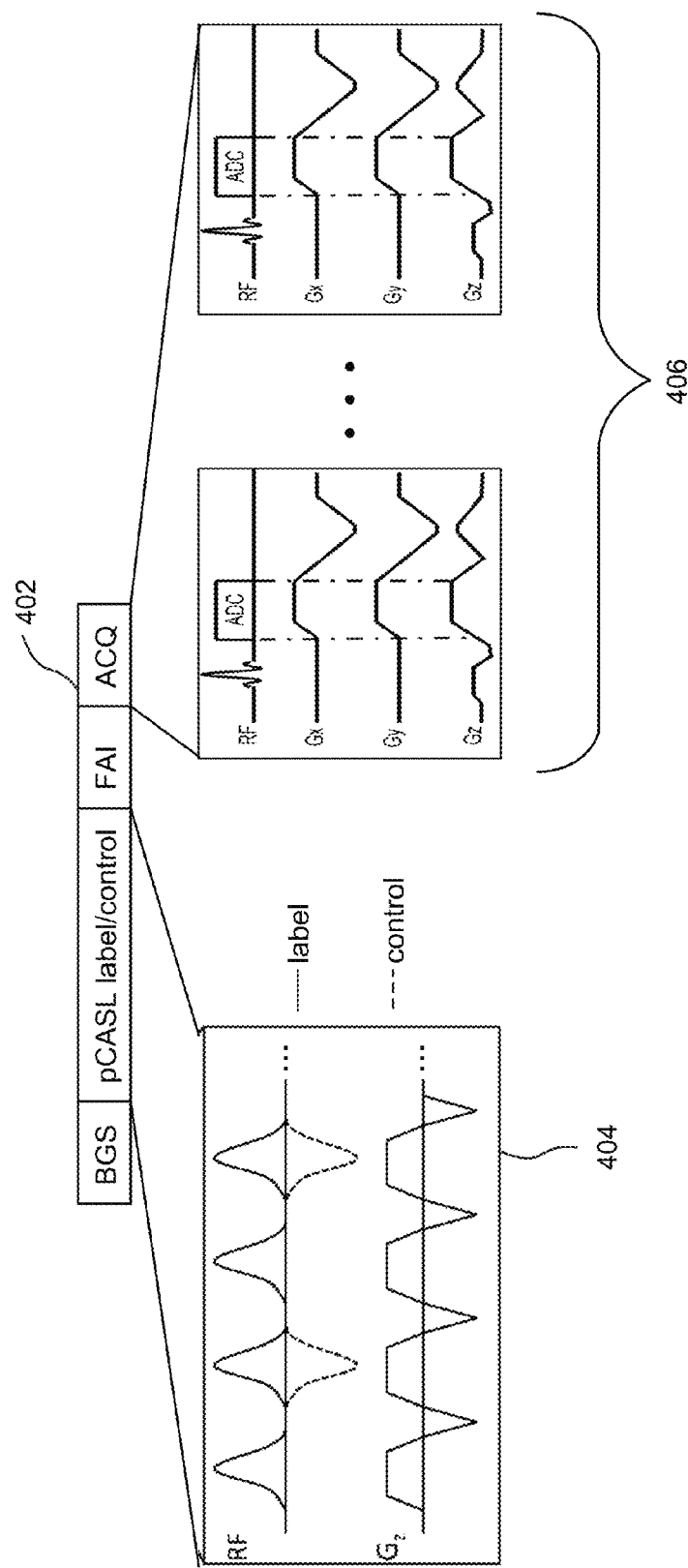
FIG. 4 illustrates an example MR acquisition sequence, in accordance with one or more embodiments.

FIG. 4 illustrates an example MR sequence 402, in accordance with one or more embodiments. MR sequence 402 may be used, for example, in operations 204 and 206 discussed above. Wu, incorporated above by reference, describes a sequence similar, or sometimes identical, to MR sequence 402.

As noted above, pCASL (and CASL angiography in general) operates by acquiring control and tagged images, and then subtracting them to obtain an angiographic image.

According to embodiments, an MR sequence 402 to label inflowing blood and acquire angiography images may include portions of the sequence, or subsequences for, background saturation, pCASL, PASL, and imaging.

Accordingly, MR sequence 402 includes a part of the sequence which performs the pCASL control and labeling by causing appropriate RF pulses and gradients. An example train of pCASL label/control RF pulses and gradients is shown in 404.

As shown in 404, the pCASL label/control portion of MR sequence 402 comprises a train of RF pulses for labeling and control. For labeling, as described in Wu, the RF phase cycling may be set such that RF pulses with the same phase are performed on the labeling plane (e.g. labeling plane 304 shown in FIG. 3), so that spins passing through labeling plane may undergo adiabatic inversion. In the control state, the RF pulse train and the gradients may be the same as in the label state, while the RF phase is cycled such that spins at the labeling plane see RF pulses having a phase of $\pi$ relative to the previous pulse, leading to limited effect on the passing spins. In an embodiment, as in Wu, the pCASL label/control subsequence may be 1-3 seconds in duration, with 500 microsecond pulses with 1200 microseconds between pulses. In various embodiments, pCASL parameters such as the number of RF pulses in the pulse train for labeling and control, the corresponding pulses (e.g., amplitude, shape, etc.), and inter-pulse gap, gradients, and the like may be configurable.

As shown in sequence 402, the pCASL label/control is preceded by a background suppression stage. Background suppression is directed, for example, to reduce the signal from background tissue. In the example shown in FIG. 3, for example, background suppression includes reducing the signal from cerebrospinal fluid. Background suppression may be achieved using conventional techniques, such as, for example, selectively inverting the imaging area (e.g., imaging slab 302). An example technique for background suppression that may be used in embodiments is described in Wu. In some embodiments, background suppression may be optional.

Optionally, at the end of the pCASL label/control, and before image acquisition, a technique such as flow-alternating inversion recovery (FAIR), as described in Wu, may be used to reduce the signal loss that may occur due to inflowing fresh spin during image data acquisition.

An image acquisition subsequence follows the pCASL label/control. An exemplary image acquisition subsequence is shown in 406. As shown, a series of acquisitions may follow the pCASL label/control subsequence. Each acquisition in 406, according to embodiments, includes an RF excitation pulse selectively applied, followed by data acquisition in kx, ky, kz dimensions and corresponding analog-to-digital (ADC) conversion, as described in Barger et al., "Time-resolved contrast-enhanced imaging with isotropic resolution and broad coverage using an undersampled 3D projection trajectory," Magnetic Resonance in Medicine, 48:297-305, 2002, which is hereby incorporated by reference in its entirety. Each acquisition illustrated in 406 corresponds to one radial line of points in the spherical volume, in the direction (from the origin) as specified by the corresponding x, y, z gradient strength. One or multiple full or partial projection(s) of points can also be acquired. Thus, the series of respective acquisitions shown in 406, obtains a k-space data set corresponding to a subset of radial trajectories that intersect the origin of k-space, as for example, shown in FIG. 5.

Figure 5:
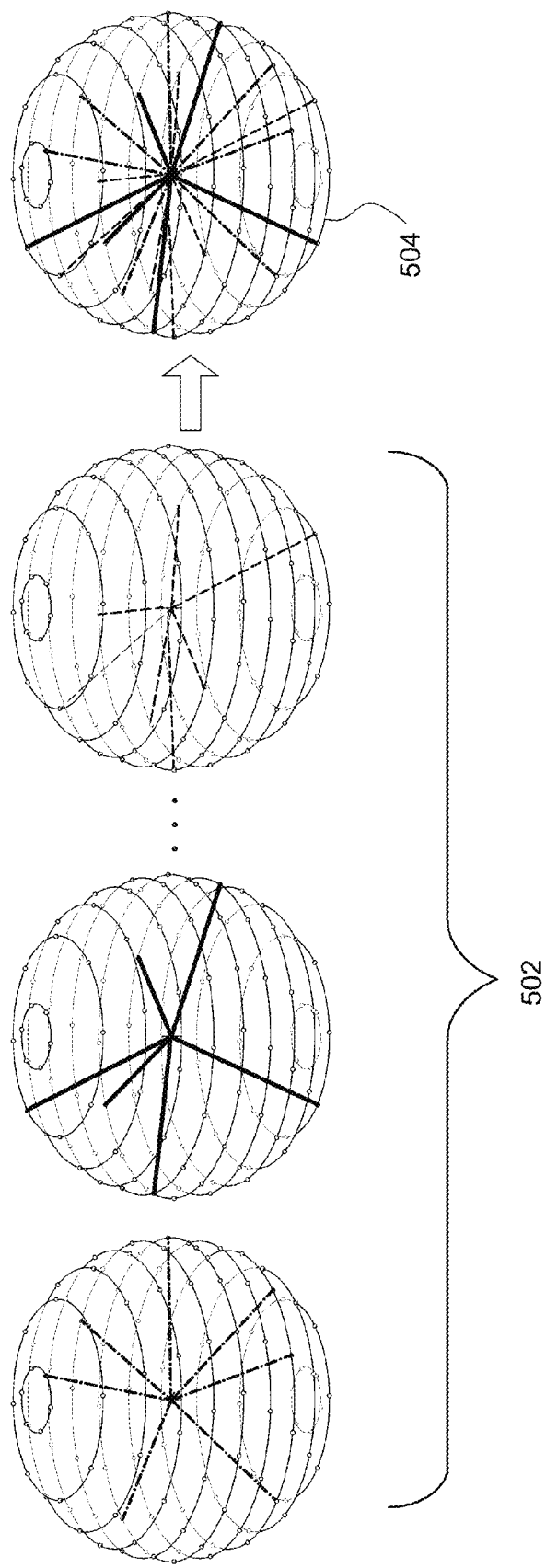
FIG. 5 schematically illustrates example distribution of radial lines of k-space data acquisitions, in accordance with one or more embodiments.

FIG. 5 schematically illustrates example distribution of radial lines of k-space data acquisitions in spherical volumes, in accordance with one or more embodiments.

Each spherical volume in 502 illustrates an instance of k-space in 3D, with each point in the respective spherical volumes corresponding to a value in k-space. The lines in each spherical volume 502 represent samples of k-space values along radial lines that each intersect the k-space center (also referred to as "origin"). In each spherical volume 502, the illustrated radial lines are substantially evenly distributed throughout the entire k-space. Ideally, the radial lines in each spherical volume 502 would be precisely evenly distributed in order to cover the entire k-space. However, depending on configuration parameters such as, for example, a number of radial lines desired in a spherical volume and/or an interleave angle for the radial lines, some amount of variance from an even distribution of the radial lines may be expected and tolerated in embodiments. The highest degrees of accuracy of the motion correction and/or the clarity of the motion-corrected images may be achieved with highly evenly distributed radial lines covering the entire k-space. Although denser distributions of radial lines may lead to improve the low resolution image, and consequently the accuracy of motion correction in embodiments, longer scan time may compromise the benefit due to higher possibility of motion distortion within the respective acquisitions.

Spherical volume 504 illustrates the aggregation of the spherical volumes 502.

While certain embodiments have been described, these embodiments have been presented by way of example only and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging (MRI) system for effecting magnetic resonance (MR) images with reduced motion artifacts, said MRI system comprising:
    an MRI gantry including a static magnetic field coil, gradient magnetic field coils, at least one radio frequency (RF) coil configured to transmit RF signals into an imaging volume and/or to receive nuclear magnetic resonance (NMR) RF signals from an object located in the imaging volume; and
    at least one digital data processor coupled to receive digitized MR data from said at least one RF coil, said at least one processor being configured to:
    acquire a plurality of k-space data sets, each k-space data set being acquired by traversing a plurality of radial trajectories of locations in three-dimensional (3D) k-space;
    generate a plurality of 3D MR images, each 3D MR image derived from a k-space populated by a respective one of the k-space data sets;
    align the 3D MR images with respect to each other;
    determine one or more motion parameters for the object based upon the aligning;
    modify, using the determined one or more motion parameters, values of at least one of the acquired k-space data sets;
    generate a motion-corrected 3D MR image by constructing it from a set of corrected sets of acquired k-space data including the modified values; and
    output the motion-corrected 3D MR image to a display, a data storage, or to a data transmission port.

2. The MRI system of claim 1, further comprising:
    a sequence controller configured to apply an MR sequence comprising a plurality of labeling pulses to the object,
    wherein each of the acquired k-space data sets is acquired after a respective application of the plurality of labeling pulses.

3. The MRI system of claim 2, wherein the MR sequence comprises at least one background suppression radio frequency pulse preceding the plurality of labeling pulses.

4. The MRI system of claim 2, wherein the MR sequence includes a pseudo-continuous arterial spin labeling (PCASL) sequence.

5. The MRI system of claim 1, further comprising an interface for configuring the MR sequence performed by the sequence controller.

6. The MRI system of claim 1, wherein respective ones of the radial trajectories include a center of k-space.

7. The MRI system of claim 6, wherein said each of the radial trajectories include the origin location of k-space.

8. The MRI system of claim 1, further comprising an interface for configuring one or more parameters for 3D radial acquisitions,
wherein for each k-space data set, the traversed plurality of radial trajectories correspond to the configured one or more parameters.

9. The MRI system of claim 8, wherein the configured one or more parameters include at least one pattern for three dimensional radial acquisitions,
wherein for each k-space data set, the traversed plurality of radial trajectories correspond to the at least one pattern.

10. The MRI system of claim 1, wherein each of the k-space data sets under samples k-space.

11. The MRI system of claim 1, wherein said each k-space data set comprises radial trajectories substantially evenly distributed throughout k-space.

12. A magnetic resonance imaging (MRI) method for effecting magnetic resonance (MR) images with reduced motion artifacts, said MRI method comprising:
placing an object into an MRI gantry including a static magnetic field coil, gradient magnetic field coils, at least one radio frequency (RF) coil configured to transmit RF signals into an imaging volume and/or to receive nuclear magnetic resonance (NMR) RF signals from said object when located in the imaging volume;
acquiring a plurality of k-space data sets, each k-space data set being acquired by traversing a plurality of radial trajectories of locations in three-dimensional (3D) k-space;
generating a plurality of 3D MR images, each 3D MR image derived from a k-space populated by a respective one of the k-space data sets;
aligning the 3D MR images with respect to each other;
determining one or more motion parameters for the object based upon the aligning;
modifying, using the determined one or more motion parameters, values of at least one of the acquired k-space data sets;
generating a motion-corrected 3D MR image by constructing it from a set of corrected sets of acquired k-space data including the modified values; and
outputting the motion-corrected 3D MR image to a display, a data storage, or to a data transmission port.

13. A non-transitory computer readable storage medium, having executable computer program instructions recorded thereon, which when executed by at least one processor of a magnetic resonance imaging (MRI) system having an MRI gantry including a static magnetic field coil, gradient magnetic field coils, at least one radio frequency (RF) coil configured to transmit RF signals into an imaging volume and/or to receive nuclear magnetic resonance (NMR) RF signals from an object located in the imaging volume, causes the at least one processor to generate a diagnostic image having reduced motion artifacts, by performing operations comprising:
acquiring a plurality of k-space data sets, each k-space data set being acquired by traversing a plurality of radial trajectories of locations in three-dimensional (3D) k-space;
generating a plurality of 3D MR images, each 3D MR image derived from a k-space populated by a respective one of the k-space data sets;
aligning the 3D MR images with respect to each other;
determining one or more motion parameters for the object based upon the aligning;
modifying, using the determined one or more motion parameters, values of at least one of the acquired k-space data sets;
generating a motion-corrected 3D MR image by constructing it from a set of corrected sets of acquired k-space data including the modified values; and
outputting the motion-corrected 3D MR image to a display, a data storage, or to a data transmission port.

* * * * *